United States Patent [19]

Nestor et al.

[11] 4,234,571
[45] Nov. 18, 1980

[54] NONAPEPTIDE AND DECAPEPTIDE DERIVATIVES OF LUTEINIZING HORMONE RELEASING HORMONE

[75] Inventors: John J. Nestor, San Jose; Gordon H. Jones; Brian H. Vickery, both of Cupertino, all of Calif.

[73] Assignee: Syntex (U.S.A.) Inc., Palo Alto, Calif.

[21] Appl. No.: 47,661

[22] Filed: Jun. 11, 1979

[51] Int. Cl.³ .................... A61K 37/00; C07C 103/52
[52] U.S. Cl. ............................. 424/177; 260/112.5 LH
[58] Field of Search ............... 260/112.5 LH; 424/177

[56] References Cited
U.S. PATENT DOCUMENTS

| | | | |
|---|---|---|---|
| 3,992,530 | 11/1976 | Foell et al. | 260/112.5 LH |
| 4,005,194 | 1/1977 | Johnson | 424/177 |
| 4,010,125 | 3/1977 | Schally et al. | 260/112.5 LH |
| 4,018,726 | 4/1977 | Schally et al. | 260/112.5 LH |
| 4,086,219 | 4/1978 | Wittle et al. | 260/112.5 LH |
| 4,089,946 | 5/1978 | Foell et al. | 260/112.5 LH |
| 4,143,133 | 3/1979 | Foell et al. | 260/112.5 LH |

*Primary Examiner*—Delbert R. Phillips
*Attorney, Agent, or Firm*—Alan M. Krubiner; Tom M. Moran

[57] ABSTRACT

Nonapeptide and decapeptide analogs of LH-RH of the formula (pyro)Glu-His-V-Ser-W-X-Y-Arg-Pro-Z     (I)

and the pharmaceutically acceptable salts thereof wherein:

V is tryptophyl, phenylalanyl or 3-(1-naphthyl)-L-alanyl;
W is tyrosyl, phenylalanyl or 3-(1-pentafluorophenyl)-L-alanyl;
X is a D-amino acid residue

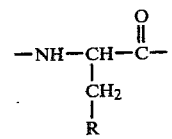

wherein R is
(a) a carbocyclic aryl-containing radical selected from the group consisting of naphthyl, anthryl, fluorenyl, phenanthryl, biphenylyl, benzhydryl and phenyl substituted with three or more straight chain lower alkyl groups; or
(b) a saturated carbocyclic radical selected from the group consisting of cyclohexyl substituted with three or more straight chain lower alkyl groups, perhydronaphthyl, perhydrobiphenylyl, perhydro-2,2-diphenylmethyl and adamantyl;

Y is leucyl, isoleucyl, nor-leucyl or N-methyl-leucyl;
Z is glycinamide or —NH—R¹, wherein
R¹ is lower alkyl, cycloalkyl, fluoro lower alkyl or

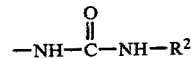

wherein
R² is hydrogen or lower alkyl,
are disclosed. These compounds exhibit potent LH-RH agonist properties.

15 Claims, No Drawings

NONAPEPTIDE AND DECAPEPTIDE DERIVATIVES OF LUTEINIZING HORMONE RELEASING HORMONE

BACKGROUND OF THE INVENTION

Luteinizing hormone (LH) and follicular stimulating hormone (FSH) are released from the anterior pituitary gland under the control of the releasing hormone LH-RH produced in the hypothalamic region. LH and FSH act on the gonads to stimulate the synthesis of steroid hormones and to stimulate gamete maturation. The pulsatile release of LH-RH, and thereby the release of LH and FSH, controls the reproductive cycle in domestic animals and humans. Additionally, LH-RH has effects in placenta, in releasing HCG, and directly on the gonads. Agonist analogs of LH-RH are useful for the control of fertility by two mechanisms of action. Low doses of LH-RH analogs can stimulate ovulation and are useful in the treatment of hypothalamic and ovulatory infertility. Additionally they can be used for hypogonadal conditions and impotence, and stimulate spermatogenesis and androgen production in the male. Paradoxically, larger doses of highly potent and long-lasting analogues of LH-RH have an opposite effect and block ovulation in the female and suppress spermatogenesis in the male. Related to these effects is a suppression of normal circulating levels of sexual steroids of gonadal origin, including reduction in accessory organ weight in the male and the female. In domestic animals this paradoxical effect promotes weight gain in a feedlot situation, stimulates abortion in pregnant animals and in general, acts as a chemical sterilant.

The natural hormone releasing hormone LH-RH is a decapeptide comprised of naturally occurring amino acid (which have the L-configuration except for the achiral amino acid glycine). Its sequence is as follows: (pyro) Glu-His-Trp-Ser-Tyr-Gly-Leu-Arg-Pro-Gly-NH$_2$. Many analogues of this natural material have been studied and the very large majority of them have proven to be of insufficient biological activity to be clinically useful. Certain select modifications have proven to have a beneficial effect on biological activity. By far the most significant modification is obtained by changing the 6-position residue from Gly to a D-amino acid. For example, replacing the Gly residue in the 6-position by D-Ala, D-Leu, D-Phe or D-Trp has led to a series of analogues of LH-RH with increased activity relative to LH-RH. See M. Monahan, et al, *Biochem.*, 12, 4616 (1973) for [D Ala$^6$]-LHRH; J. A. Vilchez-Martinez, et al, *Biochem. Biophys. Res. Comm.*, 59, 1226 (1974) for [D-Leu$^6$]LHRH and desGly$^{10}$[D-Leu$^6$, Pro NHEt$^9$]LHRH; D. H. Coy, et al, *J. Med. Chem.*, 19, 423 (1976) for$^6$[D-Phe]LHRH; and W. Vale, et al, *Clinical Endocrinology*, 5th Supp., Blackwell Scientific Publications, Oxford, England (1976), p. 2615 and D. H. Coy, et al; *Biochem. Biophys. Res. Comm.*, 67, 576 (1979) for [D-Trp$^6$]LHRH.

In addition to the substantial increases in activity obtained by the above-referred to substitutions in position 6, further increases in activity may be obtained by eliminating the Gly-NH$_2$ in position 10 to afford a nonapeptide as an alkyl-, cycloalkyl- or fluoroalkylamide, or by replacing Gly-NH$_2$ by an α-azaglycine amide. See for example, M. Fujino, et al, *Biochem. Biophys. Res. Comm.*, 49, 863 (1972), D. H. Coy, et al, *Biochem.* 14, 1848 (1975) and A. S. Dutta, et al, *J. Chem. Soc. Perkin I*, 1979, 379.

Substitution of N-methyl-leucine for the leucine residue in position 7 leads to increased stability towards enzymatic degradation. See for example, N. Ling, et al, *Biochem Biophys. Res. Comm.*, 63, 801 (1975).

Substitution of the tryptophan residue in position 3 by 3-(1-naphthyl)-L-alanine leads to an increase in biological potency. See for example, K.U. Prasad, et al, *J. Med. Chem.*, 19, 492 (1976) and Y. Yabe, *Chem. Pharm. Bull.*, 24 (12), 3149 (1976).

The tyrosine residue in position 5 can be replaced by phenylalanine or 3-(1-pentafluorophenyl)-L-alanine with the retention of substantial biological activity. See for example, N. Yanaihara, et al, *Biochem. Biophys. Res. Comm.*, 52, 64 (1973), and D. Coy, et al, *J. Med. Chem.*, 16, 877 (1973).

It would be desirable to prepare further analogues of LH-RH which have even a higher degree of biological activity than those heretofore described and which can be used clinically in animals and humans.

SUMMARY OF THE INVENTION

The present invention refers to novel nonapeptide and decapeptide derivatives of LH-RH which have, in the 6-position, certain lipophilic D-amino acids. The invention is also directed to various methods of use of these compounds and to pharmaceutical compositions therefor. A further aspect of the invention involves processes for the preparation of the novel compounds described above and to intermediates useful in such processes.

DETAILED DESCRIPTION OF THE INVENTION

The present invention relates to novel nonapeptide and decapeptide derivatives of LH-RH. More particularly the present invention relates to derivatives of LH-RH which have, in the 6-position, specific unnatural D-amino acid residues containing lipophilic carbocyclic residues, particularly residues containing two or more carbocyclic aryl (or perhydroaryl) rings or a phenyl (or cyclohexyl) ring which is highly alkyl substituted.

More specifically the compounds of the present invention are nonapeptides and decapeptides of the formula

(pyro)Glu-His-V-Ser-W-X-Y-Arg-Pro-Z  (I)

and the pharmaceutically acceptable salts thereof wherein:

V is tryptophyl, phenylalanyl or 3-(1-naphthyl)-L-alanyl;

W is tyrosyl, phenylalanyl or 3-(1-pentafluorophenyl)-L-alanyl;

X is a D-amino acid residue

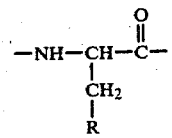

wherein R is
(a) a carbocyclic aryl-containing radical selected from the group consisting of naphthyl, anthryl, fluorenyl, phenanthryl, biphenylyl, benzhydryl and phenyl substituted with three or more straight chain lower alkyl groups; or (b) a saturated carbocyclic radical selected from the group consisting of cyclohexyl substituted with three or more straight chain lower alkyl groups, perhydronaphthyl, perhydrobiphenylyl, perhydro-2,2-diphenylmethyl and adamantyl;

Y is leucyl, isoleucyl, nor-leucyl or N-methyl-leucyl;

Z is glycinamide or -NH-R$^1$, wherein

R$^1$ is lower alkyl, cycloalkyl, fluoro lower alkyl or

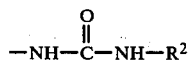

wherein

R$^2$ is hydrogen or lower alkyl.

As set forth above and for convenience in describing this invention, the conventional abbreviations for the various common amino acids are used as generally accepted in the peptide art as recommended by the IUPAC-IUB Commission on Biochemical Nomenclature, *Biochemistry*, 11, 1726 (1972) and represent L-amino acids with the exception of the achiral amino acid glycine and with the further exception of the amino acids in the 6-position designated by X. All peptide sequences mentioned herein are written according to the generally accepted convention whereby the N-terminal amino acid is on the left and the C-terminal amino acid is on the right.

As used herein, the term "pharmaceutically acceptable salts" refer to salts that retain the desired biological activity of the parent compound and do not impart any undesired toxicological effects. Examples of such salts are (a) acid addition salts formed with inorganic acids, for example hydrochloric acid, hydrobromic acid, sulfuric acid, phosphoric acid, nitric acid and the like; and salts formed with organic acids such as, for example, acetic acid, oxalic acid, tartaric acid, succinic acid, maleic acid, fumaric acid, gluconic acid, citric acid, malic acid, ascorbic acid, benzoic acid, tannic acid, pamoic acid, alginic acid, polyglutamic acid, naphthalenesulfonic acids, naphthalenedisulfonic acids, polygalacturonic acid; (b) salts with polyvalent metal cations such as zinc, calcium, bismuth, barium, magnesium, aluminum, copper, cobalt, nickel, cadmium, and the like; or with an organic cation formed from N, N'-dibenzylethylene-diamine or ethylenediamine; or (c) combinations, of (a) and (b), e.g. a zinc tannate salt and the like.

As used herein the term "lower alkyl" refers to a straight or branched chain saturated hydrocarbon group having from 1 to 4 carbon atoms such as, for example, methyl, ethyl, n-propyl, isopropyl, n-butyl, isobutyl, sec-butyl and tert-butyl; the term "cycloalkyl group" refers to a cyclic saturated hydrocarbon group having from 3 to 6 carbon atoms, for example cyclopropyl, cyclobutyl, cyclopentyl and cyclohexyl; the term "fluoro lower alkyl" refers to a lower alkyl group wherein one or more hydrogen atoms are replaced by fluorine, such as, for example, trifluoromethyl, pentafluoroethyl, 2,2,2-trifluoroethyl, and the like.

As used herein "naphthyl" is inclusive of 1- and 2-naphthyl; "anthryl" is inclusive of 1-, 2- and 9-anthryl; "fluorenyl" is inclusive of 2-,3-,4- and 9-fluorenyl; "phenanthryl" is inclusive of 2-,3-, and 9-phenanthryl; and "adamantyl" is inclusive of 1- and 2-adamantyl.

Preferred compounds of this invention are those wherein X is 3-(2-naphthyl)-D-alanyl or 3-(2,4,6-trimethylphenyl)-D-alanyl; Z is glycinamide or —NHEt; V is tryptophyl or phenylalanyl; W is tyrosyl and Y is leucyl or N-methyl-leucyl. Particularly preferred compounds are (pyro) Glu-His-Trp-Ser-Tyr-3-(2-naphthyl)-D-alanyl-Leu-Arg-Pro-Gly-NH$_2$, (pyro) Glu-His-Trp-Ser-Tyr-3-(2-naphthyl)-D-alanyl-N-methyl-Leu-Arg-Pro-Gly-NH$_2$, (pyro)Glu-His-Phe-Ser-Tyr-3-(2-naphthyl)-D-alanyl-Leu-Arg-Pro-Gly-NH$_2$, (pyro) Glu-His-Trp-Ser-Tyr-3-(2,4,6-trimethylphenyl)-D-alanyl-Leu-Arg-Pro-Gly-NH$_2$, (pyro) Glu-His-Trp-Ser-Tyr-3-(2-(naphthyl)-D-alanyl-Leu-Arg-Pro-NHEt, and (pyro) Glu-His-Trp-Ser-Tyr-3-(2-naphthyl)-D-alanyl-N-methyl-Leu-Arg-Pro-NHEt, and their pharmaceutically acceptable salts.

Especially preferred is (pyro)Glu-His-Trp-Ser-Tyr-3-(2-naphthyl)-D-alanyl-Leu-Arg-Pro-Gly-NH$_2$ and its salts.

The compounds of this invention and, particularly, the salts thereof, exhibit surprisingly potent and long lasting LH-RH agonist activity in comparison to the previously most potent LH-RH agonists, namely (pyro)Glu-His-Trp-Ser-Tyr-D-Trp-Ser-Arg-Pro-Gly-HN$_2$ and the corresponding prolylethylamide. A primary measure of potency is the ability to partially or completely suppress estrus in normally cycling adult female rats (determined over a 2 week period) by twice daily subcutaneous injection.

Other bioassays which have been used for LH-RH analogues and which have been used for compounds of the present invention include:

(a) ovulation induction in diestrous or proestrous female rats by subcutaneous injection (Rippel, et al, *Proc. Soc. Exp. Biol. Med.*, 148, 1193(1975)), (b) LH and FSH release by dispersed anterior pituitary cell cultures as measured by radioimmunoassay (Vale, et al, *Endocrinology*, 91, 562(1972)), and (c) LH and FSH release into the peripheral circulation of ovariectomized, steroid treated rats in response to intravenous injection as measured by radioimmunoassay (Arimura, et al, *Endocrinology*, 90, 163(1972)).

On a more advanced level, activity for these compounds may be demonstrated in vivo by depression of spermatogenesis and circulating and testicular levels of testosterone as well as dramatic reduction in prostate size in dogs suffering from benign prostatic hypertrophy.

As a result of the above the compounds may find use in a large variety of situations where control of LH and FSH, or direct gonadal action is important, including:

PHYSIOLOGICAL UTILITIES (LOW DOSE EFFECTS)

ovulation induction in anovulatory infertility and for timed ovulation in female mammals;

therapy for infertility due to insufficient luteal function in women;

therapy for hypogonadotrophic or hypogonadal infertility in either sex-human.

therapy for cystic ovary/nymphomania syndrome in cattle;

induction or enhancement of sexual behaviour or therapy for importence/frigidity.

PARADOXICAL UTILITIES (HIGH DOSE EFFECTS)

female contraception;
ovulation suppression or delay;
induction of parturition;
synchronization of ovulation;
estrus suppression;
growth promotion in female animals;
luteolysis, menses induction;
early, first trimester abortifacient;
therapy for endometriosis;
therapy for mammary tumors and cysts therapy for polycystic ovary syndrome (Stein-Leventhal);
therapy for uterine carcinoma;
therapy for benign prostatic hypertrophy and for prostatic carcinoma;
male contraception;
therapy for diseases which result from excessive gonadal hormone production in either sex;
 functional castration in male food producing animals;
suppression of proestrous discharge.

Another aspect of the present invention relates to particular uses for the above-described compounds, (including uses not heretofore described for LH-RH analogues) namely their uses for inhibiting ovulation (i.e. contraception) in the female, in the management of endometriosis, in the treatment of benign prostatic hypertrophy and in the inhibition of spermatogenesis (i.e. contraception) in the male. Thus, in these aspects, the invention is directed to a method useful for inhibition of ovulation, management of endometriosis, reduction of prostate size or inhibition of spermatogenesis in a mammalian subject having need of or desiring, said treatment which comprises administering to said subject an effective amount of a compound of the present invention as hereinabove described or a pharmaceutical composition containing same.

In the practice of the method of this invention an effective amount of a compound of the invention or a pharmaceutical composition containing same is administered to the subject in need of, or desiring, such treatment. These compounds or compositions may be administered by any of a variety of routes depending upon the specific end use, including orally, parenterally (including subcutaneous, intramuscular and intravenous administration), vaginally (particularly for contraception), rectally, buccally (including sublingually), or intranasally. The most suitable route in any given case will depend upon the use, particular active ingredient, the subject involved, and the judgment of the medical practitioner. The compound or composition may also be administered by means of slow-release, depot or implant formulations as described more fully hereinbelow.

In general for the uses hereinabove described, which are so-called "paradoxical" or high-dose uses, it is expedient to administer the active ingredient in amounts between about 0.01 and 100 µg/kg body weight per day, preferably between about 0.1 and 5.0 µg/kg body weight per day. This administration may be accomplished by a single daily administration, by distribution over several applications or by slow release in order to achieve the most effective results.

The exact dose and regimen for administration of these compounds and compositions will necessarily be dependent upon the needs of the individual subject being treated, the type of treatment, the degree of affliction or need and, of course, the judgment of the medical practitioner. In general, parenteral administration requires lower dosage than other methods of administration which are more dependent upon absorption.

A further aspect of the present invention relates to pharmaceutical compositions containing as active ingredient a compound of the present invention which compositions comprise such compound in admixture with a pharmaceutically acceptable, non-toxic carrier. As mentioned above, such compositions may be prepared for use for parenteral (subcutaneous, intramuscular or intravenous) administration particularly in the form of liquid solutions or suspensions; for use in vaginal or rectal administration particularly in semisolid forms such as creams and suppositories; for oral or buccal administration particularly in the form of tablets or capsules; or intranasally particularly in the form of powders, nasal drops or aerosols.

The compositions may conveniently be administered in unit dosage form and may be prepared by any of the methods well-known in the pharmaceutical art, for example as described in Remington's Pharmaceutical Sciences, Mack Publishing Company, Easton, PA., 1970. Formulations for parenteral administration may contain as common excipients sterile water or saline, polyalkylene glycols such as polyethylene glycol, oils of vegetable origin, hydrogenated naphthalenes and the like. Formulations for vaginal or rectal administration, e.g. suppositories, may contain as excipients, for example, polyalkyleneglycols, vaseline, cocoa butter, and the like. Formulations for inhalation administration may be solid and contain as excipients, for example, lactose or may be aqueous or oily solutions for administration in the form of nasal drops. For buccal administration typical excipients include sugars, calcium stearate, magnesium stearate, pregelatinated starch, and the like.

It is particularly desirable to deliver the compounds of the present invention to the subject over prolonged periods of time, for example, for periods of one week to one year from a single administration. Various slow release, depot or implant dosage forms may be utilized. For example, a dosage form may contain a pharmaceutically acceptable non-toxic salt of the compound which has a low degree of solubility in body fluids, for example, (a) an acid addition salt with a polybasic acid such as phosphoric acid, sulfuric acid, citric acid, tartaric acid, tannic acid, pamoic acid, alginic acid, polyglutamic acid, naphthalene mono- or di-sulfonic acids, polygalacturonic acid, and the like; (b) a salt with a polyvalent metal cation such as zinc, calcium, bismuth, barium, magnesium, aluminum, copper, cobalt, nickel, cadmium and the like, or with an organic cation formed from e.g., N,N'-dibenzylethylenediamine or ethylenediamine; or (c) combinations of (a) and (b) e.g. a zinc tannate salt. Additionally, the compounds of the present invention or, preferably, a relatively insoluble salt such as those just described, may be formulated in a gel, for example, an aluminum monostearate gel with, e.g. sesame oil, suitable for injection. Particularly preferred salts are zinc salts, zinc tannate salts, pamoate salts, and the like. Another type of slow release depot formulation for injection would contain the compound or salt dispersed or encapsulated in a slow degrading, non-toxic, non-antigenic polymer such as a polylactic acid/polyglycolic acid polymer for example as described in U.S. Pat. No. 3,773,919. The compounds or, preferably, relatively insoluble salts such as those described above may also be formulated in cholesterol matrix silastic pellets, particularly for use in animals. Additional slow release, depot or implant formulations, e.g. liposomes, are well known in the literature. See, for example, "Sustained and Controlled Release Drug Delivery Systems", J. R. Robinson ed., Marcel Dekker, Inc., New York, 1978. Particular reference with respect to LH-RH type compounds may be found, for example, in U.S. Pat. No. 4,010,125.

The polypeptides of the present invention may be synthesized by any techniques that are known to those skilled in the peptide art. An excellent summary of the many techniques so available may be found in J. M. Stewart and J. D. Young, "Solid Phase Peptide Synthesis", W. H. Freeman Co., San Francisco, 1969, and J. Meienhofer, "Hormonal Proteins and Peptides", Vol. 2, p. 46., Academic Press (New York), 1973 for solid phase peptide synthesis and E. Schroder and K. Lubke, "The Peptides", Vol. 1, Academic Press (New York), 1965 for classical solution synthesis.

In general, these methods comprise the sequential addition of one or more amino acids or suitably protected amino acids to a growing peptide chain. Normally, either the amino or carboxyl group of the first amino acid is protected by a suitable protecting group. The protected or derivatized amino acid can then be either attached to an inert solid support or utilized in solution by adding the next amino acid in the sequence having the complimentary (amino or carboxyl) group suitably protected, under conditions suitable for forming the amide linkage. The protecting group is then removed from this newly added amino acid residue and the next amino acid (suitably protected) is then added, and so forth. After all the desired amino acids have been linked in the proper sequence, any remaining protecting groups (and any solid support) are removed sequentially or concurrently, to afford the final polypeptide. By simple modification of this general procedure, it is possible to add more than one amino acid at a time to a growing chain, for example, by coupling (under conditions which do not racemize chiral centers) a protected tripeptide with a properly protected dipeptide to form, after deprotection, a pentapeptide.

A particularly preferred method of preparing compounds of the present invention involves solid phase peptide synthesis.

In this particularly preferred method the α-amino function of the amino acids is protected by an acid or base sensitive group. Such protecting groups should have the properties of being stable to the conditions of peptide linkage formation, while being readily removable without destruction of the growing peptide chain or racemization of any of the chiral centers contained therein. Suitable protecting groups are t-butyloxycarbonyl (Boc), benzyloxycarbonyl (Cbz), biphenylisopropyloxycarbonyl, t-amyloxycarbonyl, isobornyloxycarbonyl, α,α-dimethyl-3,5-dimethoxybenzyloxycarbonyl, o-nitrophenylsulfenyl, 2-cyano-t-butyloxycarbonyl, 9-fluorenylmethyloxycarbonyl and the like, especially t-butyloxycarbonyl (Boc).

Particularly preferred side chain protecting groups are, for arginine:nitro, p-toluenesulfonyl, 4-methoxybenzenesulfonyl, Cbz, Boc and adamantyloxycarbonyl; for tyrosine:benzyl, o-bromobenzyloxycarbonyl, 2,6-dichlorobenzyl, isopropyl, cyclohexyl, cyclopentyl and acetyl; for serine:benzyl and tetrahydropyranyl; for histidine:benzyl, p-toluenesulfonyl and 2,4-dinitrophenyl.

The C-terminal amino acid is attached to a suitable solid support. Suitable solid supports useful for the above synthesis are those materials which are inert to the reagents and reaction conditions of the stepwise condensation-deprotection reactions, as well as being insoluble in the media used. Suitable solid supports are chloromethylpolystyrene-divinylbenzene polymer, hydroxymethyl-polystyrene-divinylbenzene polymer, and the like, especially chloromethyl-polystyrene-1% divinylbenzene polymer. For the special case where the C-terminus of the compound will be glycinamide, a particularly useful support is the benzhydrylaminopolystyrene-divinylbenzene polymer described by P. Rivaille, et al, Helv. Chim. Acta., 54, 2772 (1971). The attachment to the chloromethyl polystyrene-divinylbenzene type of resin is made by means of the reaction of the $N^\alpha$-protected amino acid, especially the Boc-amino acid, as its cesium, tetramethylammonium, triethylammonium, 4,5-diazabicyclo[5.4.0]undec-5-ene, or similar salt in ethanol, acetonitrile, N,N-dimethylformamide (DMF), and the like, especially the cesium salt in DMF, with the chloromethyl resin at an elevated temperature, for example between about 40° and 60° C., preferably about 50° C., for from about 12 to 48 hours, preferably about 24 hours. The $N^\alpha$-Boc-amino acid is attached to the benzhydrylamine resin by means of an N,N'-dicyclohexylcarbodiimide (DCC)/1-hydroxybenzotriazole (HBT) mediated coupling for from about 2 to about 24 hours, preferably about 12 hours at a temperature of between about 10° and 50° C., preferably 25° C. in a solvent such as dichloromethane or DMF, preferably dichlormethane. The coupling of successive protected amino acids can be carried out in an automatic polypeptide synthesizer as is well known in the art. The removal of the $N^\alpha$-protecting groups may be performed in the presence of, for example, a solution of trifluoroacetic acid in methylene chloride, hydrogen chloride in dioxane, hydrogen chloride in acetic acid, or other strong acid solution, preferably 50% trifluoroacetic acid in dichloromethane at about ambient temperature. Each protected amino acid is preferably introduced in approximately 2.5 molar excess and the coupling may be carried out in dichloromethane, dichloromethane/DMF mixtures, DMF and the like, especially in methylene chloride at about ambient temperature. The coupling agent is normally DCC in dichloromethane but may be N,N'-di-iso-propylcarbodiimide or other carbodiimide either alone or in the presence of HBT, N-hydroxysuccinimide, other N-hydroxyimides or oximes. Alternately, protected amino acid active esters (e.g. p-nitrophenyl, pentafluorophenyl and the like) or symmetrical anhydrides may be used.

At the end of the solid phase synthesis the fully protected polypeptide is removed from the resin. When the linkage to the resin support is of the benzyl ester type, cleavage is by means of aminolysis with an alkylamine or fluoroalkylamine for peptides with a proline C-terminus, or by aminolysis with, for example, ammonia/methanol or ammonia/ethanol for peptides with a glycine C-terminus at a temperature between about 10° and 50° C., preferably about 25° C., for between about 12 and 24 hours preferably about 18 hours. Alternatively, the peptide may be removed from the resin by transesterification, e.g., with methanol, followed by aminolysis. The protected peptide may be purified at this point by silica gel chromatography. The removal of the (side chain) protecting groups from the polypeptide is performed by treating the aminolysis product with, for example, anhydrous liquid hydrogen fluoride in the presence of anisole or other carbonium scavenger, treatment with hydrogen fluoride/pyridine complex, treatment with tris(trifluoroacetyl)boron and trifluoroacetic acid, by reduction with hydrogen and palladium on carbon or polyvinylpyrrolidone, or by reduction with sodium in liquid ammonia, preferably with liquid hydrogen fluoride, and anisole at a temperature between about −10° and +10° C., preferably about 0° C., for between about 15 minutes and 1 hour, preferably about 30 minutes. For the glycine terminal peptides on the benzhydrylamine resins, the resin cleavage and deprotection steps may be combined in a single step utilizing liquid hydrogen fluoride and anisole as described above. The fully deprotected polypeptide is then purified by a sequence of chromatographic steps employing any or all of the following types: ion exchange on a weakly basic resin in the acetate form; hydrophobic adsorption chromatography on underivatized polystyrene-divinylbenzene (for example Amberlite XAD); silica gel adsorption chromatography; ion exchange chromatography on carboxymethylcellulose; partition chromatography, e.g. on Sephadex G-25, or countercurrent distribution; high performance liquid chromatography (HPLC), especially reverse phase HPLC on octyl- or octadecylsilyl-silica bonded phase column packing.

If a racemic amino acid is used in the 6-position, the diastereomeric nonapeptide or decapeptide final products are separated, and the desired peptide containing a D-amino acid in the 6-position is isolated and purified, preferably during the above-described chromatographic process.

The preparation of peptides having C-terminal azaglycine amides is preferably done using classical peptide solution synthesis using known peptide intermediates. This is described in more detail in Example 3.

Thus, in another aspect the present invention relates to a method for preparing compounds of the formula (pyro)Glu-His-V-Ser-W-X-Y-Arg-Pro-Z    (I)

and the pharmaceutically acceptable salts thereof wherein:

V is tryptophyl, phenylalanyl or 3-(1-naphthyl)-L-alanyl;

W is tyrosyl, phenylalanyl or 3-(1-pentafluorophenyl)-1-alanyl;

X is a D-amino acid residue

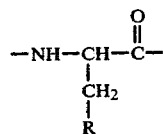

wherein R is (a) a carbocyclic aryl-containing radical selected from the group consisting of naphthyl, anthryl, fluorenyl, phenanthryl, biphenylyl, benzhydryl and phenyl substituted with three or more straight chain lower alkyl groups; or (b) a saturated carbocyclic radical selected from the group consisting of cyclohexyl substituted with three or more straight chain lower alkyl groups, perhydronaphthyl, perhydrobiphenylyl, perhydro-2,2-diphenylmethyl and adamantyl;

Y is leucyl, isoleucyl, nor-leucyl or N-methyl-leucyl;

Z is glycinamide or —NH—R$^1$, wherein
R$^1$ is lower alkyl, cycloalkyl, fluoro lower alkyl or

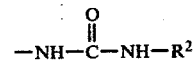

wherein
R$_2$ is hydrogen or lower alkyl. which process comprises:

(i) removing protecting groups and, optionally, covalently bound solid support from a protected polypeptide to afford a compound of Formula (I) or a salt thereof, and optionally (ii) converting a compound of Formula (I) to a pharmaceutically acceptable salt, or (iii) converting a salt of a compound of Formula (I) to a pharmaceutically acceptable salt, or (iv) decomposing a salt of a compound of Formula (I) to a free polypeptide of Formula (I).

The following examples are given to enable those skilled in the art to more fully understand the practice the present invention. They should not be construed as a limitation upon the scope of the invention, but merely as being illustrative and representative thereof.

PREPARATION A

To an oven dried flask containing 0.1 L. of absolute ethanol (distilled from magnesium ethoxide) was added 1.52 g. of sodium metal. When hydrogen evolution ceased, 10.21 g. of ethyl 2-acetamido-2-cyanoacetate and 13.26 g. of 2-bromomethylnaphthalene were added to the solution. The solution was heated at reflux for 1 hour and then cooled. The ethanol was removed under reduced pressure and the residue was taken up in ethyl acetate. The organic layer was washed with two 50 mL. portions of water, one 50 mL. portion of saturated sodium chloride solution, and was dried over magnesium sulfate. The solution was filtered, the solvent was stripped off at reduced pressure and the residue was hydrolyzed in 100 mL. of concentrated hydrochloric acid at reflux for 2 hours.

The hydrolysis mixture was cooled and the precipitate of crude product was filtered. The crude product was redissolved in 0.5 L. of hot water containing 5 mL. of concentrated hydrochloric acid treated with charcoal, and the pH of the solution was adjusted to 6 with concentrated ammonium hydroxide. The precipitate was filtered and dried in vacuo to yield 11.3 g. of pure 3-(2-naphthyl)-D,L-alanine of melting point 230°–232° C.

Repeating the above procedure, substituting a stoichiometrically equivalent amount of
1-bromomethylnaphthalene,
9-bromomethylanthracene,
9-bromomethylfluorene,
2-bromomethylfluorene,
2-bromomethylanthracene,
1-bromomethylanthracene,
α-chloroisodurene,
4-bromomethylbiphenyl,
1-bromomethyladamantane,
3-bromomethylphenanthrene
1-chloromethyl-2,4,6-tri-(n-butyl)benzene, and
1-chloromethyl-2,3,4,5,6-pentamethylbenzene,
for 2-bromomethylnaphthalene there are obtained the following amino acids:
3-(1-naphthyl)-D,L-alanine, m.p. 185°–187° C., 3-(9-anthryl)-D,L-alanine, m.p. 290° C. (HCl salt),
3-(9-fluorenyl)-D,L-alanine,
3-(2-fluorenyl)-D,L-alanine, m.p. 264°-269° C.,
3-(2-anthryl)-D,L-alanine,
3-(1anthryl)-D, L-alanine,
3-(2,4,6-trimethylphenyl)-D,L-alanine, m.p. 235°-237° C.,
3-(4-biphenylyl)-D,L-alanine, m.p. 290° C.,
3-(1-adamantyl)-D,L-alanine,
3-(3-phenanthryl)D,L-alanine,
3-(2,4,6-tri(n-butyl)phenyl)-D,L-alanine and
3-(2,3,4,5,6-pentamethylphenyl)-D,L-alanine, respectively.

PREPARATION B

A solution of 18.2 g. 1,1-diphenylethylene, 25.3 g. methyl α-methoxy-N-benzyloxycarbonylglycinate, and 1.5 g. 2-naphthalenesulfonic acid in 300 mL. dry benzene was refluxed for 2 days. The crude product was purified on a column of silicic acid using a gradient of $CH_2Cl_2$ to $CH_2Cl_2$/EtOAc (18:1). The purified methyl 2-[1-(2,2-diphenylethylenyl)]-N-benzyloxycarbonylglycinate was hydrolyzed to the corresponding acid with a solution of 10.9 g KOH in 350 mL. of 10% aqueous methanol. The resultant crude acid was dissolved in 100 mL. of 95% ethanol containing 3 mL. of conc. HCl and hydrogenated in the presence of 2 g. of 10% Pd on carbon for 24 hours to yield 2.4 g. of 3-(2,2-diphenylmethyl)-D,L-alanine, m.p. 235°-237° C.

PREPARATION C

To a solution of 12.9 g. of 3-(2-naphthyl)-D,L-alanine in 120 mL. of 1 M NaOH was added 6.23 mL. of acetic anhydride and 60 mL of 1 M NaOH during ½ hour at 0° C. The pH was adjusted to 2 with conc. HCl and the resultant precipitate was filtered. The solid was recrystallized from 60% aqueous ethanol to yield 12.2 g. of N-acetyl-3-(2-naphthyl)-D,L-alanine.

To a solution of 15 g. of this N-acetyl amino acid in 240 mL. of dry methanol was added 15.8 mL. of boron trifluoride etherate and the mixture was refluxed for 1 hour. The alcohol was evaporated, 200 mL water was added and the solution was extracted with ethyl acetate. The organic layer was washed with aqueous base and acid, dried over $MgSO_4$, filtered, and stripped to an oil. Crystallization of this oil from ethyl acetate/hexane gave 14.2 g. of methyl N-acetyl-3-(2-naphthyl)-D,L-alaninate, m.p. 79°-80° C.

Repeating the above procedure, substituting a stoichiometrically equivalent amount of
3-(1-naphthyl)-D,L-alanine,
3-(2-fluorenyl)-D,L-alanine,
3-(2-anthryl)-D,L-alanine,
3-(1-anthryl)-D,L-alanine, and
3-(2,2-diphenylmethyl)-D,L-alanine
for 3-(2-naphthyl)-D,L-alanine there are obtained
methyl N-acetyl-3-(1-naphthyl)-D,L-alaninate, m.p. 97.5°-98° C.,
methyl N-acetyl-3-(2-fluorenyl)-D,L-alaninate, m.p. 170°-171° C.,
methyl N-acetyl-3-(2-anthryl)-D,L-alaninate, and
methyl N-acetyl-3-(2,2-diphenylmethyl)-D,L-alaninate, m.p. 113°-114° C., respectively.

PREPARATION D

A solution of 6.6 g. of methyl N-acetyl-3-(2-naphthyl)-D,L alaninate in a mixture of 300 mL. of dimethylsulfoxide, 120 mL. of 1 M KCl and 780 mL. of $H_2O$ was treated with 33.6 mg. of the enzyme subtilisin in 3 mL. of 0.1 M KCl. The pH was maintained at 7 by means of automatic titration with 0.2 M NaOH by a Radiometer pH stat. After 30 minutes 70 mL. of NaOH solution had been taken up and the hydrolysis was stopped. The solution was made basic with 12 g. $NaHCO_3$ and was extracted with ethyl acetate. The organic layer contained methyl N-acetyl-3-(2-naphthyl)-D-alaninate. Crystallization from ethyl acetate/hexane gave a yellow solid, m.p. 80°-81° C.

This was converted to the free amino acid and then to the N-Boc amino acid as follows:

A solution of 2.5 g of methyl N-acetyl-3-(2-naphthyl)-D-alaninate in 60 ml of 6 N HCl was heated at 120°-130° for 3 hours and cooled to room temperature. The white precipitate which formed was collected and recrystallized from 50 ml of $H_2O$ containing 1 ml of 12 N HCl by neutralization with $NH_4OH$ to pH 6, and dried in vacuo to yield 1.2 g of 3-(2-naphthyl)-D-alanine, m.p. 242°-244°, $[\alpha]_D^{25}$ 26.6° (c 0.5, $CH_3CO_2H$).

A stirred solution of 3-(2-naphthyl)-D-alanine in a mixture of 55 ml of 1 N NaOH, 10 ml $H_2O$, and 20 ml dioxane was treated with 1.48 g of di-tert-butyl dicarbonate and 0.22 g of magnesium oxide at 0°. After 1.5 hours an additional 0.3 g of di-tert-butyl dicarbonate was added and the mixture was allowed to come to room temperature. The solid was removed by filtration and the filtrate was concentrated to 50 ml. This aqueous solution was brought to pH 2.5 with $NaHSO_4$ and extracted with ethyl acetate. The organic layer was washed with 5% $NaHSO_4$, water and saturated salt solution. The ethyl acetate solution was dried over magnesium sulfate, filtered and concentrated to an oil which was crystallized from ether/hexane to yield 1.3 g of N-Boc 3-(2-naphthyl)-D-alanine, m.p. 90°-91°, $[\alpha]_D^{25}$ −32.6° (c 0.8, MeOH).

Repeating the above procedure substituting a stoichiometrically equivalent amount of
methyl N-acetyl-3-(1-naphthyl)-D,L-alaninate,
methyl N-acetyl-3-(2-fluorenyl)-D,L-alaninate,
methyl N-acetyl-3-(2-anthryl)-D,L-alaninate, and
methyl N-acetyl-3-(2,2-diphenylmethyl)-D,L-alaninate
for methyl N-acetyl-3-(2-naphthyl)-D,L-alaninate there are obtained the following $N^\alpha$-Boc amino acids, via the corresponding free amino acids:
N-Boc-3-(1-naphthyl)-D-alanine, m.p. 92°-93° C., $[\alpha]_D^{25}$ 54.8° (c 0.5 MeOH),
N-Boc-3-(2-fluorenyl)-D-alanine, m.p. 161°-163° C. (dec.),
N-Boc-3-(2-anthryl)-D-alanine, and N-Boc-3-(2,2-diphenylmethyl)-D-alanine, m.p. 153°-154° C., respectively.

PREPARATION E

In a Parr hydrogenation bottle was placed 0.85 g. of 3-(2-naphthyl)-D-alanine, 100 ml. of 2 M hydrochloric acid, and 0.85 g. of Adam's catalyst ($PtO_2$). The solution was packed under 60 lb/in$^2$ of $H_2$ gas for 20 hours in a Parr hydrogenation apparatus. The mixture was heated to dissolve the white precipitate and was filtered through diatomaceous earth. Concentration of the solution at reduced pressure followed by lyophilization from water yielded 0.8 g. of 3-(2-perhydronaphthyl)-D-alanine as a white solid of mp 230°-232° C.

This material was dissolved in a mixture of 3.2 ml. 1 N-NaOH, 5 ml. water, and 15 ml. dioxane, and was treated with 0.14 g MgO and 0.85 g. di-tert-butyldicarbonate. After 1 hour at 0° C. and 2 hours at 25° C. the suspension was filtered, concentrated to dryness at reduced pressure, the residue dissolved in water, washed with diethyl ether, and acidified to pH2 with NaHSO$_4$. The acidified aqueous layer was extracted three times with ethyl acetate and the extracts were combined, dried over MgSO$_4$, filtered, and concentrated to give 0.75 g. of N-Boc-3-(2-perhydronaphthyl)-D-alanine as white oil.

A 0.1 g. portion of this material was dissolved in 5 ml tetrahydrofuran and titrated at 0° C. with freshly prepared diazomethane until the bright yellow color persisted. The reaction was quenched with 1 ml acetic acid, the solvent was evaporated and the residue was partitioned between 75 ml. ethyl acetate and 75 ml. water. The organic layer was washed with 5% NaHCO$_3$, water, 5% NaHSO$_4$, water, saturated NaCl solution, and dried over MgSO$_4$. The solution was filtered, concentrated under reduced pressure, and loaded on a preparative thin layer chromatography plate (750μ thick, silica gel, 20×20 cm.). The plate was developed with dichloromethane/ethyl acetate (18/1) and the product band was removed. The silica gel from the product band was washed with dichloromethane/ethyl acetate (9:1) on a fritted glass funnel and the filtrate was concentrated to give 0.1 g. of methyl N-Boc-3-(2-perhydronaphthyl)-D-alaninate as a light yellow oil.

This material was obtained as a mixture of two isomers at the 2 position of the perhydronaphthalene nucleus. These diastereomeric compounds may be separated on a high performance liquid chromatography column (Lichrosorb silica gel 60, 5 micron) with ethyl acetate/hexane (1:9) as eluent and hydrolyzed to the free acid, N-Boc-3-(2-perhydronaphthyl)-D-alanine.

Repeating the above procedure substituting a stoichiometrically equivalent amount of
3-(1-naphthyl)-D-alanine,
3-(2,2-diphenylmethyl)-D-alanine,
3-(2,4,6-trimethylphenyl)-D,L-alanine,
3-(4-biphenylyl)-D,L-alanine,
3-(2,4,6-tri(n-butyl)phenyl)-D,L-alanine, and
3-(2,3,4,5,6-pentamethylphenyl)-D,L-alanine,
for 3-(2-naphthyl)-D-alanine there are obtained the following N-Boc amino acids:
N-Boc-3-(1-perhydronaphthyl)-D-alanine,
N-Boc-3-(perhydro-2,2-diphenylmethyl)-D-alanine,
N-Boc-3-(2,4,6-trimethylcyclohexyl)-D,L-alanine,
N-Boc-3-(perhydro-4-biphenylyl)-D,L-alanine,
N-Boc-3-(2,4,6-tri(n-butyl)cyclohexyl)-D,L-alanine, and
N-Boc-3-(2,3,4,5,6-pentamethylcyclohexyl)-D,L-alanine, respectively.

EXAMPLE 1

In the reaction vessel of a Beckman 990 Peptide Synthesizer was placed 0.8 g. (0.8 mmol.) of benzhydrylamino-polystyrene-divinylbenzene resin (Lab Systems, Inc.) as described by Rivaille, supra. Amino acids were added sequentially to this resin by means of a synthesis program, as follows:

| Step | | | |
|---|---|---|---|
| 1 | CH$_2$Cl$_2$ wash | 1 time | 1.5 min |
| 2 | 50% CF$_3$CO$_2$H/CH$_2$Cl$_2$ deprotection | 1 time | 1.5 min |
| 3 | 50% CF$_3$CO$_2$H/CH$_2$Cl$_2$ deprotection | 1 time | 30 min |
| 4 | CH$_2$Cl$_2$ wash | 3 times | 1.5 min |
| 5 | 10% triethylamine/CH$_2$Cl$_2$ | 2 times | 1.5 min |
| 6 | CH$_2$Cl$_2$ wash | 3 times | 1.5 min |
| 7 | N$^\alpha$-Boc-amino acid solution | 1 time | add |
| 8 | N,N'-dicyclohexylcarbodiimide solution | 1 time | add |
| 9 | CH$_2$Cl$_2$ rinse and hold coupling | 1 time | coupling reaction 2 hr |
| 10 | CH$_2$Cl$_2$ rinse add | 1 time | 1.5 min |
| 11 | CH$_2$Cl$_2$ wash | 3 times | 1.5 min |
| 12 | ethanol wash | 3 times | 1.5 min |
| 13 | CH$_2$Cl$_2$ wash | 3 times | 1.5 min |

Steps 1–13 complete a coupling cycle for one amino acid and completeness of the reaction is checked by the ninhydrin method of E. Kaiser, et al., *Anal. Biochem.*, 34, 595 (1970).

The resin was coupled sequentially with a 2.5 molar excess of each protected amino acid and DCC. Thus, the resin was treated during successive coupling cycles with
0.433 g. Boc-Gly-OH,
0.432 g. Boc-Pro-OH,
0.857 g. Boc-Arg(Tosyl)-OH,
0.462 g. Boc-Leu-OH,
0.504 g. Boc-3-(2-naphthyl)-D-alanine and 0.272 g. 1-hydroxybenzotriazole,
0.724 g. N-Boc,O-2-bromobenzoyloxycarbonyl-L-tyrosine,
0.59 g. Boc-Ser(Benzyl)-OH,
0.608 g. Boc-Trp-OH,
0.654 g. Boc-His(Tosyl)-OH, and
0.524 g. pyroglutamic acid.

The resin was removed from the reaction vessel, washed with CH$_2$Cl$_2$, and dried in vacuo to yield 2.0 g. of protected polypeptide resin.

The polypeptide product was simultaneously removed from the resin and completely deprotected by treatment with anhydrous liquid HF. A mixture of 2.0 g. of protected polypeptide resin and 2 mL. of anisole (scavenger) in a Kel-F reaction vessel was treated with 20 mL. of redistilled (from CoF$_3$) anhydrous liquid HF at 0° C. for 30 minutes. The HF was evaporated under vacuum and the residue of (pyro)-Glu-His-Trp-Ser-Tyr-3-(2-naphthyl)-D-alanyl-Leu-Arg-Pro-Gly-NH$_2$, as its HF salt, was washed with ether. The residue was then extracted with glacial acetic acid. The acetic acid extract was lyophilized to yield 0.8 g. of crude material.

The crude polypeptide was loaded on a 4×40 cm. Amberlite XAD-4 column (polystyrene-4% divinylbenzene copolymer) and eluted with a concave gradient from water (0.5 L.) to ethanol (1 L.). The tubes containing fractions from effluent volume 690 mL. to 1,470 mL. were pooled and stripped to dryness to yield 490 mg. of partially purified polypeptide.

A 150 mg. sample of the partially purified product was subjected to partition chromatography on a 3×50 cm. column of Sephadex G-25 using the solvent system 1-butanol/toluene/acetic acid/water containing 1.5% pyridine in the ratios 10:15:12:18. The pure fractions were pooled on the basis of thin layer chromatography (silica gel; BuOH/H$_2$O/HOAc/EtOAc; 1:1:1:1) and HPLC (5 micron, reverse phase, octadecylsilyl packing; 40% 0.03 M NH$_4$OAc/60% acetonitrile). The desired product came off the column in fractions from effluent volume 1,000 mL. to 1,400 mL. (Rf 0.1). The pure fractions were pooled, stripped to dryness, taken up in H$_2$O, and lyophilized to yield 57 mg of pure pyro-glutamylhistidyl-tryptophylseryl-tyrosyl-3-(2-naphthyl)-D-alanyl-leucyl-arginylprolyl-glycinamide, as its acetic acid addition salt, $[\alpha]_D^{25} -27.4°$ (c 0.9, HOAc), m.p. 185°–193° C. (dec.).

EXAMPLE 2

For the synthesis of analogues with a C-terminal Pro-NH-CH$_2$CH$_3$, a synthesis program identical to that described in Example 1 was used. The Beckman 990 Synthesizer reaction vessel was loaded with 2.13 g. of Boc-Pro-O-Resin, prepared by the reaction of equimolar ratios of the dry cesium salt of Boc-Pro-OH with chloromethyl-polystyrene/1% divinylbenzene (Lab Systems, Inc.). The quantity of Boc-Pro-O-Resin taken contained 1.4 mmol. of proline.

The resin was coupled sequentially with a 2.5 molar excess of each protected amino acid and DCC. Thus, the resin was reacted during successive coupling cycles with
1.61 g. Boc-Arg(Tosyl)-OH,
0.93 g. Boc-Leu-OH.H$_2$O,
0.94 g. Boc-3-(2-naphthyl)-D-alanine and 0.49 g. of 1-hydroxybenzotriazole,
1.75 g. N-Boc-O-2-bromobenzyloxycarbonyl-L-tyrosine, and 1.11 g. Boc-Ser(Benzyl)-OH.

At this point in the synthesis the quantity of protected polypeptide resin was split in half and one half was carried through to completion by sequential reaction with
0.57 g. Boc-Trp-OH,
0.77 g. Boc-His(Tosyl)-OH, and
0.21 g. pyroglutamic acid.

The resin was removed from the reaction vessel, washed with CH$_2$Cl$_2$, and dried in vacuo to yield 2.26 g. of protected polypeptide resin.

The protected polypeptide was cleaved from the resin by aminolysis with 25 mL. of ethylamine for 18 hours at 2° C. The ethylamine was allowed to evaporate and the resin was extracted with methanol. The methanol was evaporated to yield 1.39 g. of pyro-Glu-His(-Tosyl)-Trp-Ser(Benzyl)-Tyr(2-bromobenzyloxycarbonyl)-3-(2-naphthyl)-D-alanyl-Leu-Arg(Tosyl)-Pro-NH-CH$_2$CH$_3$.

The crude polypeptide was deprotected by treatment with a mixture of 3 mL. anisole and 30 mL. redistilled (from CoF$_3$) anhydrous liquid HF at 0° C. for 30 minutes in a Kel-F reaction vessel. The HF was evaporated under vacuum and the residue was washed with ether. The residue was dissolved in 2 M acetic acid and lyophilized to yield 0.82 g. of crude (pyro)-Glu-His-Trp-Ser-Tyr-3-(2-naphthyl)-D-alanine-Leu-Arg-Pro-NH-CH$_2$CH$_3$ as its acetic acid addition salt. Final purification was achieved by preparative high performance liquid chromatography of a 20 mg. sample on a 0.9×550 mm. column of 40–50μ. octadecylsilylated silica (Merck, Lichroprep C$_{18}$). The eluant was 64% 0.03 M NH$_4$OAc/36% acetonitrile. In four runs a total of 61 mg. of crude material was purified. After three lyophilizations from water, 15 mg. of pure pyroglutamyl-histidyl-tryptophyl-seryl-tyrosyl-3-(2-naphthyl)-D-alanyl-leucyl-arginyl-proline ethylamide was obtained as its acetic acid addition salt, m.p. 180°–190° C., $[\alpha]_D^{25} -57.2°$ (C 1.1, HOAc).

Repeating the above cleavage, substituting a stoichiometric amount of:
n-butylamine,
cyclopropylamine,
cyclohexylamine,
trifluoromethylamine,
pentafluoroethylamine, and
2,2,2-trifluoroethylamine
for ethylamine there are obtained the corresponding
n-butylamide,
cyclopropylamide,
cyclohexylamide,
trifluoromethylamide,
pentafluoroethylamide, and
2,2,2-trifluoroethylamide
of the aforementioned nonapeptide.

EXAMPLE 3

Compounds of Formula I wherein Z is $$-NH-\overset{\overset{O}{\|}}{C}NH-R^2$$

may be prepared by classical solution synthesis.

For example, the following approach may be used wherein "AzaGlyNH$_2$" is

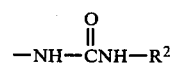

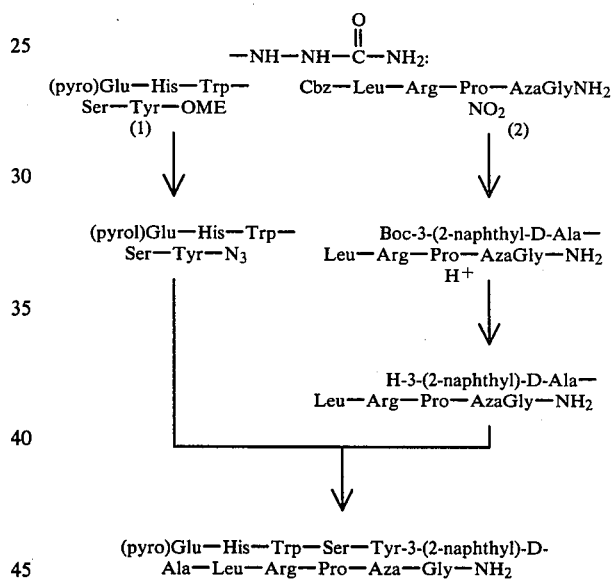

as the free peptide or salt.

The coupling of the individual fragments may proceed by the acyl azide method (J. Honzel, et al, *Coll. Czech. Chem. Comm,* 26, 2333 (1971)), by DCC/HBT coupling or other racemization free fragment coupling techniques. Compounds (1) and (2) are known (M. Fujino, et al, *Biochem. Biophys. Res. Comm.,* 57, 1248 (1974) and A. S. Dutta, et al., *J. Chem. Soc. Perkin I,* 1979, 379, respectively). Compound (3) is prepared from (2) by removal of the Cbz and nitro groups by hydrogenolysis, followed by coupling with N-Boc-3-(2-naphthyl)-D-alanine using DCC/HBT or other coupling agent known in the art. See Dutta, et al, supra, for a similar LH-RH analogue synthesis.

Similarly, utilizing other amino acids in place of N-Boc-3-(2-naphthyl)-D-alanine, other compounds of Formula I may be prepared, e.g.
(pyro)Glu-His-Trp-Ser-Tyr-3-(2-naphthyl)-D-Ala-N-methyl-Leu-Arg-Pro-AzaGlyNH$_2$ and
(pyro)Glu-His-Trp-Ser-Tyr-3-(2,4,6-trimethylphenyl)-D-Ala-Leu-Arg-Pro-AzaGlyNH$_2$. Also, in the preparation of compound (2), use of AzaGly-NH-lower alkyl in place of Aza-Gly-NH₂ affords the corresponding peptide with an AzaGly-NH-lower alkyl terminus, e.g.

(pyro)Glu-His-Trp-Ser-Tyr-3-(2-naphthyl)-D-Ala-Leu-Arg-Pro-AzaGly-Et, (pyro)Glu-His-Trp-Ser-Tyr-3-(2-naphthyl)-D-Ala-N-methyl-Leu-Arg-Pro-AzaGly-Et and (pyro)Glu-His-Trp-Ser-Tyr-3-(2,4,6-trimethylphenyl)-D-Ala-Leu-Arg-Pro-AzaGly-Et.

EXAMPLE 4

Repeating the procedure of Example 1 and utilizing either a D-amino acid or a D,L amino acid at position 6 (in the latter case, separating the diastereomeric peptides during chromatography), substituting the appropriate amino acids in the solid phase synthesis sequence, there may be obtained the following decapeptides which are isolated and characterized as their acetic acid addition salts:

pyro-glutamyl-histidyl-tryptophyl-seryl-tyrosyl-3-(2-naphthyl)D-alanyl-N-methylleucyl-arginyl-prolyl-glycinamide;

pyro-glutamyl-histidyl-phenylalanyl-seryl-tyrosyl-3-(2-naphthyl)-D-alanyl-leucyl-arginyl-prolyl-glycinamide;

pyro-glutamyl-histidyl-3-(1-naphthyl)-L-alanyl-seryl-tyrosyl-3-(2-naphthyl)-D-alanyl-leucyl-arginyl-prolyl-glycinamide;

pyro-glutamyl-histidyl-tryptophyl-seryl-phenylalanyl-3-(2-naphthyl)-D-alanyl-leucyl-arginyl-prolyl-glycinamide;

pyro-glutamyl-histidyl-tryptophyl-seryl-3-(1-pentafluorophenyl)-L-alanyl-3-(2-naphthyl)-D-alanyl-leucyl-arginyl-prolyl-glycinamide;

pyro-glutamyl-histidyl-tryptophyl-seryl-tyrosyl-3-(1-naphthyl)-D-alanyl-leucyl-arginyl-prolyl-glycinamide;

pyro-glutamyl-histidyl-tryptophyl-seryl-tyrosyl-3-(2-anthryl)-D-alanyl-leucyl-arginyl-prolyl-glycinamide;

pyro-glutamyl-histidyl-tryptophyl-seryl-tyrosyl-3-(2-fluoroenyl)-D-alanyl-leucyl-arginyl-prolyl-glycinamide;

pyro-glutamyl-histidyl-tryptophyl-seryl-tyrosyl-3-(3-phenanthryl)-D-alanyl-leucyl-arginyl-prolyl-glycinamide;

pyro-glutamyl-histidyl-tryptophyl-seryl-tyrosyl-3-(4-biphenylyl)-D-analyl-leucyl-arginyl-prolyl-glycinamide;

pyro-glutamyl-histidyl-tryptophyl-seryl-tyrosyl-3-(2,2-diphenylmethyl)-D-alanyl-leucyl-arginyl-prolyl-glycinamide;

pyro-glutamyl-histidyl-tryptophyl-seryl-tyrosyl-3-(1-adamantyl)-D-alanyl-leucyl-arginyl-prolyl-glycinamide;

pyro-glutamyl-histidyl-tryptophyl-seryl-tyrosyl-3-(2,4,6-trimethylphenyl)-D-alanyl-leucyl-arginyl-prolyl-glycinamide;

pyro-glutamyl-histidyl-tryptophyl-seryl-tyrosyl-3-[2,4,6-tri-(n-butyl)phenyl]-D-alanyl-leucyl-arginyl-prolyl-glycinamide;

pyro-glutamyl-histidyl-tryptophyl-seryl-tyrosyl-3-(2,3,4,5,6-pentamethylphenyl)-D-alanyl-leucyl-arginyl-propyl-glycinamide;

pyro-glutamyl-histidyl-tryptophyl-seryl-tyrosyl-3-(2,4,6-trimethylcyclohexyl)-D-alanyl-leucyl-arginyl-prolyl-glycinamide;

pyro-glutamyl-histidyl-tryptophyl-seryl-tyrosyl-3-[2,4,6-tri(n-butyl)cyclohexyl]-D-alanyl-leucyl-arginyl-prolyl-glycinamide;

pyro-glutamyl-histidyl-tryptophyl-seryl-tyrosyl-3-(perhydro-1-naphthyl)-D-alanyl-leucyl-arginyl-prolyl-glycinamide;

pyro-glutamyl-histidyl-tryptophyl-seryl-tyrosyl-3-(perhydro-2-naphthyl)-D-alanyl-leucyl-arginyl-prolyl-glycinamide;

pyro-glutamyl-histidyl-tryptophyl-seryl-tyrosyl-3-(4-perhydrobiphenylyl)-D-alanyl-leucyl-arginyl-prolyl-glycinamide;

pyro-glutamyl-histidyl-tryptophyl-seryl-tyrosyl-3-(perhydro-2,2-diphenylmethyl)-D-alanyl-leucyl arginyl-prolyl-glycinamide;

pyro-glutamyl-histidyl-tryptophyl-seryl-tyrosyl-3-(2-naphthyl)-D-alanyl-isoleucyl-arginyl-prolyl-glycinamide; and pyro-glutamyl-histidyl-tryptophyl-seryl-tyrosyl-3-(2-naphthyl)-D-alanyl-norleucyl-arginyl-prolyl-glycinamide.

EXAMPLE 5

Repeating the procedure of Example 2 and utilizing either a D-amino acid or a D,L amino acid at position 6 (in the latter case, separating the diastereomeric peptides during chromatography), substituting the appropriate amino acids in the solid phase synthesis sequence, there may be obtained the following nonapeptides which are isolated and characterized as their acetic acid addition salts:

pyro-glutamyl-histidyl-tryptophyl-seryl-tyrosyl-3-(1-naphthyl)-D-alanyl-leucyl-arginyl-proline as its ethylamide, n-butylamide, cyclopropylamide, cyclohexylamide, trifluoromethylamide, pentafluoroethylamide and 2,2,2-trifluoroethylamide, pyro-glutamyl-histidyl-phenylalanyl-seryl-tyrosyl-3-(2-naphthyl)-D-alanyl-leucyl-arginyl-proline as its ethylamide, n-butylamide, cyclopropylamide, cyclohexylamide, trifluoromethylamide, pentafluoroethylamide and 2,2,2-trifluoroethylamide, pyro-glutamyl-histidyl-3-(1-naphthyl)-L-alanyl-seryl-tyrosyl-3-(2-naphthyl)-D-alanyl-leucyl-arginyl-proline as its ethylamide, n-butylamide, cyclopropylamide, cyclohexylamide, trifluoromethylamide, pentafluoroethylamide and 2,2,2-trifluoroethylamide, pyro-glutamyl-histidyl-tryptophyl-seryl-phenylalanyl-3-(2-naphthyl)-D-alanyl-leucyl-arginyl-proline as its ethylamide, n-butylamide, cyclopropylamide, cyclohexylamide, trifluoromethylamide, pentafluoroethylamide and 2,2,2-trifluoroethylamide, pyro-glutamyl-histidyl-tryptophyl-seryl-3-(1-pentafluorophenyl-L-alanyl-3-(2-naphthyl)-D-alanyl-leucyl-arginyl-proline as its ethylamide, n-butylamide, cyclopropylamide, cyclohexylamide, trifluoromethylamide, pentafluoroethylamide and 2,2,2-trifluoroethylamide, pyro-glutamyl-histidyl-tryptophyl-seryl-tyrosyl-3-(1-anthryl)-D-alanyl-leucyl-arginyl-proline as its ethylamide, n-butylamide, cyclopropylamide, cyclohexylamide, trifluoromethylamide, pentafluoroethylamide and 2,2,2-trifluoroethylamide, pyro-glutamyl-histidyl-tryptophyl-seryl-tyrosyl-3-(2-fluorenyl)-D-alanyl-leucyl-arginyl-proline as its ethylamide, n-butylamide, cyclopropylamide, cyclohexylamide, trifluoromethylamide, pentafluoroethylamide and 2,2,2-trifluoroethylamide, pyro-glutamyl-histidyl-tryptophyl-seryl-tyrosyl-3-(3-phenanthryl)-D-alanyl-leucyl-arginyl-proline as its ethylamide, n-butylamide, cyclopropylamide, cyclohexylamide, trifluoromethylamide, pentafluoroethylamide and 2,2,2-trifluoroethylamide, pyro-glutamyl-histidyl-tryptophyl-seryl-tyrosyl-3-(4-biphenylyl)-D-alanyl-leucyl-arginyl-proline as its ethylamide, n-butylamide, cyclopropylamide, cyclohexylamide, trifluoromethylamide, pentafluoroethylamide and 2,2,2-trifluoroethylamide, pyro-glutamyl-histidyl-tryptophyl-seryl-tyrosyl-3-(2,2-diphenylmethyl)-D-alanyl-leucyl-arginyl-proline as its ethylamide, n-butylamide, cyclopropylamide, cyclohexylamide, trifluoromethylamide, pentafluoroethylamide and 2,2,2-trifluoroethylamide, pyro-glutamyl-histidyl-tryptophyl-seryl-tyrosyl-3-(1-adamantyl)-D-alanyl-leucyl-arginyl-proline as its ethylamide, n-butylamide, cyclopropylamide, cyclohexylamide, trifluoromethylamide, pentafluoroethylamide and 2,2,2-trifluoroethylamide.

pyro-glutamyl-histidyl-tryptophyl-seryl-tyrosyl-3-(2,4,6-trimethylphenyl)-D-alanyl-leucyl-arginyl-proline as its ethylamide, n-butylamide, cyclopropylamide, cyclohexylamide, trifluoromethylamide, pentafluoroethylamide and 2,2,2-trifluoroethylamide.

pyro-glutamyl-histidyl-tryptophyl-seryl-tyrosyl-[2,4,6-tri-(n-butyl)phenyl]-D-alanyl-leucyl-arginyl-proline as its ethylamide, n-butylamide, cyclopropylamide, cyclohexylamide, trifluoromethylamide, pentafluoroethylamide and 2,2,2-trifluoroethylamide, pyro-glutamyl-histidyl-tryptophyl-seryl-tyrosyl-3-(2,3,4,5,6-pentamethylphenyl)-D-alanyl-leucyl-arginyl-proline as its ethylamide, n-butylamide, cyclopropylamide, cyclohexylamide, trifluoromethylamide, pentafluoroethylamide and 2,2,2-trifluoroethylamide, pyro-glutamyl-histidyl-tryptophyl-seryl-tyrosyl-3-(2,4,6-trimethylcyclohexyl)-D-alanyl-leucyl-arginyl-proline as its ethylamide, n-butylamide, cyclopropylamide, cyclohexylamide, trifluoromethylamide, pentafluoroethylamide and 2,2,2-trifluoroethylamide, pyro-glutamyl-histidyl-tryptophyl-seryl-tyrosyl-3-[2,4,6-tri(n-butyl)cyclohexyl]-D-alanyl-leucyl-arginyl-proline as its ethylamide, n-butylamide, cyclopropylamide, cyclohexylamide, trifluoromethylamide, pentafluoroethylamide and 2,2,2-trifluoroethylamide, pyro-glutamyl-histidyl-tryptophyl-seryl-tyrosyl-3-(perhydro-1-naphthyl)-D-alanyl-leucyl-arginyl-proline as its ethylamide, n-butylamide, cyclopropylamide, cyclohexylamide, trifluoromethylamide, pentafluoroethylamide and 2,2,2-trifluoroethylamide, pyro-glutamyl-histidyl-tryptophyl-seryl-tyrosyl-3-(perhydro-2-naphthyl)-D-alanyl-leucyl-arginyl-proline as its ethylamide, n-butylamide, cyclopropylamide, cyclohexylamide, trifluoromethylamide, pentafluoroethylamide and 2,2,2-trifluoroethylamide, pyro-glutamyl-histidyl-tryptophyl-seryl-tyrosyl-3-(4-perhydrobiphenylyl)-D-alanyl-leucyl-arginyl-proline as its ethylamide, n-butylamide, cyclopropylamide, cyclohexylamide, trifluoromethylamide, pentafluoroethylamide and 2,2,2-trifluoroethylamide, pyro-glutamyl-histidyl-tryptophyl-seryl-tyrosyl-3-(perhydro-2,2-diphenylmethyl)-D-alanyl-leucyl-arginyl-proline as its ethylamide, n-butylamide, cyclopropylamide, cyclohexylamide, trifluoromethylamide, pentafluoroethylamide and 2,2,2-trifluoroethylamide, pyro-glutamyl-histidyl-tryptophyl-seryl-tyrosyl-3-(2-naphthyl)-D-alanyl-N-methylleucyl-arginyl-proline as its ethylamide, n-butylamide, cyclopropylamide, cyclohexylamide, trifluoromethylamide, pentafluoroethylamide and 2,2,2-trifluoroethylamide, pyro-glutamyl-histidyl-tryptophyl-seryl-tyrosyl-3-(2-naphthyl)-D-alanyl-isoleucyl-arginyl-proline as its ethylamide, n-butylamide, cyclopropylamide, cyclohexylamide, trifluoromethylamide, pentafluoroethylamide and 2,2,2-trifluoroethylamide, and pyro-glutamyl-histidyl-tryptophyl-seryl-tyrosyl-3-(2-naphthyl)-D-alanyl-norleucyl-arginyl-proline as its ethylamide, n-butylamide, cyclopropylamide, cyclohexylamide, trifluoromethylamide, pentafluoroethylamide and 2,2,2-trifluoroethylamide,

EXAMPLE 6

A. A solution of 0.1 g of the hydrogen fluoride salt of (pyro)Glu-His-Trp-Ser-Tyr-3-(2-naphthyl)-D-Ala-Leu-Arg-Pro-Gly-NH$_2$ (See Example 1) is dissolved in 50 mL of water and passed through a column of 50 g Dowex 3 anion exchange resin which had previously been equilibrated with acetic acid and washed with deionized water. The column is eluted with deionized water and the effluent is lyophilized to yield the corresponding acetic acid salt of (pyro)Glu-His-Trp-Ser-Tyr-3-(2-naphthyl)-D-Ala-Leu-Arg-Pro-Gly-NH$_2$, $[\alpha]_D^{25}$ −27.5° (c 0.9,. HOAc).

Repeating the above, substituting other acids for acetic acid during the equilibration of the resin, there may be obtained, for example, the corresponding salts with hydrochloric acid, hydrobromic acid, sulfuric acid, phosphoric acid, nitric acid, benzoic acid, and the like.

Similarly there may be prepared the acid addition salts of other compounds of Formula I.

B. In the case of salts of low water solubility, these may be prepared by precipitation from water utilizing the desired acid. For example:

Zinc tannate salt—a solution of 10 mg of (pyro)Glu-His-Trp-Ser-Tyr-3-(2-naphthyl)-D-Ala-Leu-Arg-Pro-Gly-NH$_2$ acetic acid salt in 0.1 mL of water was treated with a solution of 8 mg of tannic acid in 0.08 mL of 0.25 M NaOH. A solution of 5 mg of ZnSO$_4$ heptahydrate in 0.1 mL of water was immediately added to the solution of the LH-RH analogue.

The resultant suspension was diluted with 1 mL water and the precipitate was centrifuged. A supernatant was decanted and the residue was washed twice with 1 mL portions of water by centrifugation of the precipitate and decantation of the supernatant. The precipitate was dried in vacuo to yield 15 mg of the mixed zinc tannate salt of the above named LH-RH analogue.

Pamoate salt—to a solution of 50 mg (pyro)Glu-His-Trp-Ser-Tyr-3-(2-naphthyl)-D-Ala-Leu-Arg-Pro-Gly-NH$_2$ acetic acid salt in a mixture of 1.6 mL of ethanol and 0.1 mL of 0.25 M NaOH was added solution of 11 mg of pamoic acid in 0.3 mL of 0.25 M NaOH. The solvents were removed at reduced pressure and the residue was suspended in 2 mL of water, centrifuged, and the supernatant was decanted. The precipitate was washed with 1.5 mL H$_2$O, centrifuged, and the supernatant was decanted. The precipitate was dried in vacuo to yield 54 mg of the pamoate salt of the above named LH-RH analogue.

In a similar manner other salts of low water solubility may be prepared.

C. Preparation of acid addition salt from free peptide.

To a solution of 50 mg of (pyro)Glu-His-Trp-Ser-Tyr-3-(2-naphthyl)-D-Ala-Leu-Arg-Pro-Gly-NH$_2$ as the free base is added 30 mL of 1 N acetic acid. The resulting solution is lyophilized to yield 50 mg. of the acetic acid salt of the above-named LH-RH analogue.

Similarly, replacing acetic acid with other acids (in stoichiometrically equivalent amounts relative to peptide) there was obtained other acid additon salts of compounds of Formula (I), for example, the salts with hydrochloric acid, hydrobromic acid, sulfuric acid, phosphoric acid, nitric acid.

D. Preparation of salt with metal cation, e.g., zinc salt.

To a solution of 50 mg (pyro)Glu-His-Trp-Ser-Tyr-3-(2-naphthyl)-D-Ala-Leu-Arg-Pro-Gly-NH$_2$ acetic acid salt in a mixture of 0.4 mL of 0.25 M NaOH, 0.3 mL water, and 1 mL ethanol was added a solution of 15 mg of ZnSO$_4$ heptahydrate in 0.2 mL of water. The precipitate was centrifuged and the supernatant was decanted. The precipitate was washed with 1 mL of water by centrifugation and decantation of the supernatant. The precipitate was dried in vacuo to yield 48 mg of the zinc salt of the above named LH-RH analogue.

In a similar manner salts with other multivalent cations e.g. calcium, bismuth, barium, magnesium, aluminum, copper, cobalt, nickel, cadmium and the like, may be prepared.

EXAMPLE 7

A solution of 50 mg of (pyro)Glu-His-Trp-Ser-Tyr-3-(2-naphthyl)-D-Ala-Leu-Arg-Pro-Gly-NH$_2$ acetic acid salt in 25 ml of water is passed through a 50 g column of Dowex 1 (strongly basic, quaternary ammonium anion exchange resin) which had been equilibrated with NaOH solution to make the counter ion hydroxide. The column is eluted with 150 ml of water and the eluant is lyophilized to yield 45 mg of the corresponding polypeptide as the free base.

Similarly other acid additions salts of compounds of Formula (I), e.g. those mentioned in Example 6, may be converted to the corresponding free bases.

EXAMPLE 8

The following are typical pharmaceutical compositions containing, as active ingredient, an LH-RH analogue of the present invention, for example (pyro)Glu-His-Trp-Ser-Tyr-3-(2-naphthyl)-D-alanyl-Leu-Arg-Pro-Gly-NH$_2$, by itself or as a pharmaceutically acceptable salt, e.g. the acetic acid addition salt, the zinc salt, the zinc tannate salt, etc. A. Tablet formulations for buccal (e.g. sublingual) administration:

| | |
|---|---|
| 1. LH-RH Analogue | 50.0 µg |
| Compressible Sugar, USP | 96.0 mg |
| Calcium Stearate | 4.0 mg |
| 2. LH-RH Analogue | 30.0 µg |
| Compressible Sugar, USP | 98.5 mg |
| Magnesium Stearate | 1.5 mg |
| 3. LH-RH Analogue | 25.0 µg |
| Mannitol, USP | 88.5 mg |
| Magnesium Stearate, USP | 1.5 mg |
| Pregelatinized Starch, USP | 10.0 mg |
| 4. LH-RH Analogue | 200.0 µg |
| Lactose, USP | 83.3 mg |
| Pregelatinized Starch, USP | 15.0 mg |
| Magnesium Stearate, USP | 1.5 mg |

Method of Manufacture a. LH-RH Analogue is dissolved in water, a sufficient quantity to form a wet granulation when mixed with the sugar portion of the excipients. After complete mixing, the granulation is dried in a tray or fluid-bed dryer. The dry granulation is then screened to break up any large aggregates and then mixed with the remaining components. The granulation is then compressed on a standard tabletting machine to the specific tablet weight.

b. In this manufacturing method, all formulations would include 0.01% gelatin, USP. The gelatin would be first dissolved in the aqueous granulation solvent followed by the LH-RH analog. The remaining steps are as in (a) above.

Formulation 4 could also be used as a tablet for oral administration. B. Long Acting intramuscular injectable formulation.

| 1. Long Acting I.M. Injectable - Sesame Oil Gel | |
|---|---|
| LH-RH Analogue | 1.0 mg |
| Aluminum monostearate, USP | 20.0 mg |
| Sesame oil q.s. ad | 1.0 ml |

The aluminum monostearate is combined with the sesame oil and heated to 125° C. with stirring until a clear yellow solution forms. This mixture is then autoclaved for sterility and allowed to cool. The LH-RH analogue is then added aseptically with trituration. Particularly preferred LH-RH analogues are salts of low solubility, e.g. zinc salts, zinc tannate salts, pamoate salts, and the like. These exhibit exceptionally long duration of activity.

2. Long acting I.M. Injectable-Biodegradable Polymer Microcapsules

| 2. Long Acting I.M. Injectable - Biodegradable Polymer Microcapsules | |
|---|---|
| LH-RH Analogue | 1% |
| 25/75 glycolide/lactide copolymer (0.5 intrinsic viscosity) | 99% |

Microcapsules (0–150µ) of above formulation suspended in:

| | |
|---|---|
| Dextrose | 5.0% |
| CMC, sodium | 0.5% |
| Benzyl alcohol | 0.9% |
| Tween 80 | 0.1% |
| Water, purified q.s. | 100.0% |

25 mg of microcapsules would be suspended in 1.0 ml of vehicle.

C. Aqueous Solution for Intramuscular Injection

| | |
|---|---|
| LH-RH Analogue | 25 mg |
| Gelatin, nonantigenic | 5 mg |
| Water for injection q.s. ad | 100 ml |

Dissolve gelatin and LH-RH analogue in water for injection, then sterile filter solution.

D. Aqueous Solution for Nasal Administration

| LH-RH Analogue | 250 mg |
| --- | --- |
| Dextrose | 5 gm |
| Benzyl alcohol | 0.9 gm |
| Water, purified q.s. ad | 100 ml |

Dissolve LH-RH analogue, dextrose, benzyl alcohol in purified water and q.s. to volume.

E. Formulation for Rectal Administration
Suppository Vehicle for Rectal Administration

| LH-RH Analogue | 500 μg |
| --- | --- |
| Witepsol H15 | 20.0 gm |

The LH-RH analogue is combined with the molten Witepsol H15, mixed well and poured into 2 gm molds.

We claim:

1. A compound of the formula (pyro)Glu-His-V-Ser-W-X-Y-Arg-Pro-Z   (I)

and the pharmaceutically acceptable salts thereof wherein:

V is tryptophyl, phenylalanyl or 3-(1-naphthyl)-L-alanyl;

W is tyrosyl, phenylalanyl or 3-(1-pentafluorophenyl)-L-alanyl;

X is a D-amino acid residue

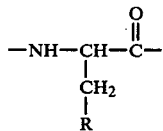

wherein R is (a) a carbocyclic aryl-containing radical selected from the group consisting of naphthyl, anthryl, fluorenyl, phenanthryl, biphenylyl, benzhydryl and phenyl substituted with three or more straight chain lower alkyl groups; or (b) a saturated carbocyclic radical selected from the group consisting of cyclohexyl substituted with three or more straight chain lower alkyl groups, perhydronaphthyl, perhydrobiphenylyl, perhydro-2,2-diphenylmethyl and adamantyl;

Y is leucyl, isoleucyl, nor-leucyl or N-methyl-leucyl;

Z is glycinamide or —NH—R¹, wherein R¹ is lower alkyl, cycloalkyl, fluoro lower alkyl or

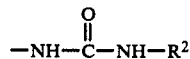

wherein
R² is hydrogen or lower alkyl.

2. The compound of claim 1 wherein V is tryptophyl or phenylalanyl; W is tyrosyl; X is 3-(2-naphthyl)-D-alanyl or 3-(2,4,6-trimethylphenyl)-D-alanyl; Y is leucyl or N-methyl-leucyl; and Z is glycin-amide or —NHEt.

3. The compound of claim 2 wherein X is 3-(2-naphthyl)-D-alanyl.

4. The compound of claim 2 which is (pyro)Glu-His-Trp-Ser-Tyr-3-(2-naphthyl)-D-alanyl-Leu-Arg-Pro-Gly-NH₂ and the pharmaceutically acceptable acid salts thereof.

5. The compound of claim 3 which is (pyro)Glu-His-Trp-Ser-Tyr-3-(2-naphthyl)-D-alanyl-N-methyl-Leu-Arg-Pro-Gly-NH₂ and the pharmaceutically acceptable salts thereof.

6. The compound of claim 3 which is (pyro)Glu-His-Trp-Ser-Tyr-3-(2-naphthyl)-D-alanyl-Leu-Arg-Pro-NHEt and the pharmaceutically acceptable salts thereof.

7. The compound of claim 3 which is (pyro)Glu-His-Trp-Ser-Tyr-3-(2-naphthyl)-D-alanyl-N-methyl-Leu-Arg-Pro-NHEt and the pharmaceutically acceptable salts thereof.

8. The compound of claim 3 which is (pyro)Glu-His-Phe-Ser-Syr-3-(2-naphthyl)-D-alanyl-Leu-Arg-Pro-Gly-NH₂ and the pharmaceutically acceptable salts thereof.

9. The compound of claim 2 wherein X is 3-(2,4,6-trimethylphenyl)-D-alanyl.

10. The compound of claim 9 which is (pyro)Glu-His-Trp-Ser-Tyr-3-(2,4,6-trimethylphenyl)-D-alanyl-Leu-Arg-Pro-Gly-NH₂ and the pharmaceutically acceptable salts thereof.

11. A method of inhibiting ovulation in a female mammalian subject which method comprises administering to said subject an effective amount of a compound of the formula (pyro)Glu-His-V-Ser-W-X-Y-Arg-Pro-Z   (I)

or a pharmaceutically acceptable salt thereof wherein:

V is tryptophyl, phenylalanyl or 3-(1-naphthyl)-L-alanyl;

W is tyrosyl, phenylalanyl or 3-(1-pentafluorophenyl)-L-alanyl;

X is a D-amino acid residue

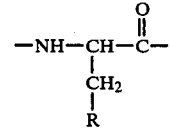

wherein R is (a) a carbocyclic aryl-containing radical selected from the group consisting of naphthyl, anthryl, fluorenyl, phenanthryl, biphenylyl, benzhydryl and phenyl substituted with three or more straight chain lower alkyl groups; or (b) a saturated carbocyclic radical selected from the group consisting of cyclohexyl substituted with three or more straight chain lower alkyl groups, perhydronaphthyl perhydrobiphenylyl, perhydro-2,2-diphenylmethyl and adamantyl;

Y is leucyl, isoleucyl, nor-leucyl or N-methyl-leucyl;

Z is glycinamide or —NH—R¹, wherein
R¹ is lower alkyl, cycloalkyl, fluoro lower alkyl or

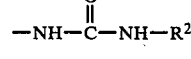

wherein
R² is hydrogen or lower alkyl, or a pharmaceutical composition containing same.

12. A pharmaceutical composition for inhibition of ovulation and treating endometriosis in a female mammalian subject and treating benign prostatic hypertrophy and inhibiting spermatogenesis in a male mammalian subject comprising an effective amount of a compound of the formula (pyro)Glu-His-V-Ser-W-X-Y-Arg-Pro-Z     (I)

or a pharmaceutically acceptable salt thereof wherein:
V is tryptophyl, phenylalanyl or 3-(1-naphthyl)-L-alanyl;
W is tyrosyl, phenylalanyl or 3-(1-pentafluorophenyl)-L-alanyl;
X is a D-amino acid residue

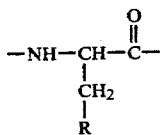

wherein R is
(a) a carbocyclic aryl-containing radical selected from the group consisting of naphthyl, anthryl, fluorenyl, phenanthryl, biphenylyl, benzhydryl and phenyl substituted with three or more straight chain lower alkyl groups; or
(b) a saturated carbocyclic radical selected from the group consisting of cyclohexyl substituted with three or more straight chain lower alkyl groups, perhydronaphthyl, perhydrobiphenylyl, perhydro-2,2-diphenylmethyl and adamantyl;
Y is leucyl, isoleucyl, nor-leucyl or N-methyl-leucyl;
Z is glycinamide or $-NH-R^1$, wherein
$R^1$ is lower alkyl, cycloalkyl, fluoro lower alkyl or

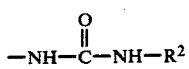

wherein
$R^2$ is hydrogen or lower alkyl, in admixture with a pharmaceutically acceptable non-toxic carrier.

13. A method of treating endometriosis in a female mammalian subject which method comprises administering to said subject an effective amount of a compound of the formula (pyro)Glu-His-V-Ser-W-X-Y-Arg-Pro-Z     (I)

or a pharmaceutically acceptable salt thereof wherein:
V is tryptophyl, phenylalanyl or 3-(1-naphthyl)-L-alanyl;
W is tyrosyl, phenylalanyl or 3-(1-pentafluorophenyl)-L-alanyl;
X is a D-amino acid residue

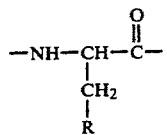

wherein R is
(a) a carbocyclic aryl-containing radical selected from the group consisting of naphthyl, anthryl, fluoroenyl, phenanthryl, biphenylyl, benzhydryl and phenyl substituted with three or more straight chain lower alkyl groups; or
(b) a saturated carbocyclic radical selected from the group consisting of cyclohexyl substituted with three or more straight chain lower alkyl groups, perhydronaphthyl, perhydrobiphenylyl, perhydro-2,2-diphenylmethyl and adamantyl;
Y is leucyl, isoleucyl, nor-leucyl or N-methyl-leucyl;
Z is glycinamide or $-NH-R^1$, wherein
$R^1$ is lower alkyl, cycloalkyl, fluoro lower alkyl or

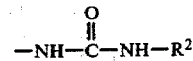

wherein
$R^2$ is hydrogen or lower alkyl, or a pharmaceutical composition containing same.

14. A method of treating benign prostatic hypertrophy in a male mammalian subject which method comprises administering to said subject an effective amount of a compound of the formula (pyro)Glu-His-V-Ser-W-X-Y-Arg-Pro-Z     (I)

or a pharmaceutically acceptable salt thereof wherein:
V is tryptophyl, phenylalanyl or 3-(1-naphthyl)-L-alanyl;
W is tyrosyl, phenylalanyl or 3-(1-pentafluorophenyl)-L-alanyl;
X is a D-amino acid residue

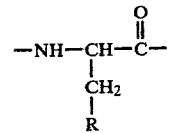

wherein R is
(a) a carbocyclic aryl-containing radical selected from the group consisting of naphthyl, anthryl, fluorenyl, phenanthryl, biphenylyl, benzhydryl and phenyl substituted with three or more straight chain lower alkyl groups; or
(b) a saturated carbocyclic radical selected from the group consisting of cyclohexyl substituted with three or more straight chain lower alkyl groups, perhydronaphthyl, perhydrobiphenylyl, perhydro-2,2-diphenylmethyl and adamantyl;
Y is leucyl, isoleucyl, nor-leucyl or N-methyl-leucyl;
Z is glycinamide or $-NH-R^1$, wherein
$R^1$ is lower alkyl, cycloalkyl, fluoro lower alkyl or

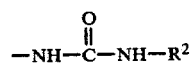

wherein
$R^2$ is hydrogen or lower alkyl, or a pharmaceutical composition containing same.

15. A method of inhibiting spermatogenesis in a male mammalian subject which method comprises administering to said subject an effective amount of a compound of the formula (pyro)Glu-His-V-Ser-W-X-Y-Arg-Pro-Z     (I)

or a pharmaceutically acceptable salt thereof wherein:
V is tryptophyl, phenylalanyl or 3-(1-naphthyl)-L-alanyl;
W is tyrosyl, phenylalanyl or 3-(1-pentafluorophenyl)-L-alanyl;

X is a D-amino acid residue

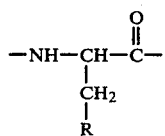

wherein R is
(a) a carbocyclic aryl-containing radical selected from the group consisting of naphthyl, anthryl, fluorenyl, phenanthryl, biphenylyl, benzhydryl and phenyl substituted with three or more straight chain lower alkyl groups; or
(b) a saturated carbocyclic radical selected from the group consisting of cyclohexyl substituted with three or more straight chain lower alkyl groups, perhydronaphthyl, perhydrobiphenylyl, perhydro-2,2-diphenylmethyl and adamantyl;

Y is leucyl, isoleucyl, nor-leucyl or N-methyl-leucyl;
Z is glycinamide or —NH—$R^1$, wherein
$R^1$ is lower alkyl, cycloalkyl, fluoro lower alkyl or

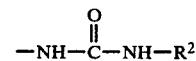

wherein
$R^2$ is hydrogen or lower alkyl, or a pharmaceutical composition containing same.

* * * * *

UNITED STATES PATENT AND TRADEMARK OFFICE

CERTIFICATE EXTENDING PATENT TERM
UNDER 35 U.S.C. 156

Patent No.     : 4,234,571

Dated          : November 18, 1980

Inventor(s)    : John J. Nestor et al

Patent Owner   : Syntex (U.S.A.) Inc.

This is to certify that there has been presented to the

COMMISSIONER OF PATENTS AND TRADEMARKS an application under 35 U.S.C. 156 for an extension of the patent term. Since it appears that the requirements of the law have been met, this certificate extends the term of the patent for the period of

2 YEARS with all rights pertaining thereto as provided by 35 USC 156 (b).

I have caused the seal of the Patent and Trademark Office to be affixed this 8th day of February, 1991.

Harry F. Manbeck, Jr.
Assistant Secretary and Commissioner
  of Patents and Trademarks